United States Patent
May

(10) Patent No.: US 7,454,974 B2
(45) Date of Patent: Nov. 25, 2008

(54) PROBE SYSTEM, ULTRASOUND SYSTEM AND METHOD OF GENERATING ULTRASOUND

(75) Inventor: Andrzej May, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 189 days.

(21) Appl. No.: 11/540,742

(22) Filed: Sep. 29, 2006

(65) Prior Publication Data

US 2008/0078249 A1   Apr. 3, 2008

(51) Int. Cl.
*G01N 9/00* (2006.01)
*G01N 29/00* (2006.01)
(52) U.S. Cl. .......................................... 73/643; 73/661
(58) Field of Classification Search ................ 73/643, 73/642, 602, 649, 661; 313/231.31; 315/111.21; 367/147, 139
See application file for complete search history.

(56) References Cited

U.S. PATENT DOCUMENTS

| | | | |
|---|---|---|---|
| 4,764,906 A * | 8/1988 | Clements et al. ............ 367/142 |
| 5,800,618 A * | 9/1998 | Niori et al. ................ 118/723 E |
| 6,509,744 B1 | 1/2003 | Biermann et al. |
| 6,591,680 B2 | 7/2003 | Batzinger et al. |
| 6,789,427 B2 | 9/2004 | Batzinger et al. |
| 6,791,280 B2 | 9/2004 | Gao et al. |
| 6,792,808 B1 | 9/2004 | Batzinger et al. |
| 7,205,700 B2 * | 4/2007 | Yamato ................... 310/313 B |
| 7,251,195 B1 * | 7/2007 | Reiff et al. ................... 367/139 |
| 7,281,491 B2 * | 10/2007 | Iwamaru ................ 118/723 E |
| 2008/0079445 A1 | 4/2008 | May |

FOREIGN PATENT DOCUMENTS

DE   19847365   5/2000
GB   2317265   3/1998

OTHER PUBLICATIONS

M. Barlow, "Modulated Plasma Audio Transducer Circuit Simplification with Power Bipolar Junction Transistors," Youngstown State University Department of Electrical and Computer Engineering, Jan. 28, 2006.

J. H. Cho et al., "Coplanar ac Discharges Between Cylindrical Electrodes With a Nanoporous Alumina Dielectric: Modular Dielectric Barrier Plasma Devices," IEEE Transactions Plasma Science, vol. 33, No. 2, Apr. 2005, pp. 378-379.

(Continued)

*Primary Examiner*—Helen C. Kwok
(74) *Attorney, Agent, or Firm*—Penny A. Clarke

(57) ABSTRACT

A probe system for initiating and stabilizing plasma discharge includes an inner conductor coupled to an AC voltage source. The probe system also includes an outer conductor arranged around the inner conductor and coupled at one end to the AC voltage source. The outer conductor forms a first electrode at another end thereof. The probe system further includes a second electrode separated from the first electrode by a gap for initiating a plasma discharge in the gap. An ultrasound probe system includes a carrier signal source for supplying a RF carrier signal, an acoustic modulator for supplying an envelope signal, and a mixer for mixing the RF carrier signal and the envelope signal to supply a modulated RF signal. The ultrasound probe system further includes a ground electrode and a RF plasma probe separated from the ground electrode by a gap and configured to receive the modulated RF signal and generate a plasma in the gap. The plasma generates ultrasound waves.

35 Claims, 7 Drawing Sheets

OTHER PUBLICATIONS

R. Rahul et al., "Optical and RF electric characteristics of atmospheric pressure open-air hollow slot microplasmas and application to bacterial inactivation," Journal of Physics D: Applied Physics, 38, 2005, pp. 1750-1759.

M. J. Colgan et al., "Very High Frequency Capacitive Plasma Sources," in High Density Plasma Sources, O. Popov, Editor, Noyes Publications, Park Ridge, New Jersey, 1995, pp. 149-190.

J. Hopwood et al., "A microfabricated atmospheric-pressure microplasma source operating in air," Journal of Physics D: Applied Physics, 38, 2005, pp. 1698-1703.

A. May et al., "Radio-frequency plasma transducer for use in harsh environments," 33rd Annual Review of Progress in Quantitative Nondestructive Evaluation, Portland, OR, 2006, pp. 1-11.

J. J. Shi et al., "Three modes in a radio frequency atmospheric pressure glow discharge," Journal of Applied Physics, vol. 94, No. 10, Nov. 2003, pp. 6303-6310.

E. Marode, "The mechanism of spark breakdown in air at atmospheric pressure between a positive point and a plane," Journal of Applied Physics, vol. 46, No. 5, May 1975, pp. 2005-2015.

D. M. Pozar, "Microwave Engineering," John Wiley and Sons, 1998, pp. 56-72.

S. Dixon et al., "Generation of ultrasound by an expanding plasma," Journal of Physics D: Applied Physics, vol. 29, 1996, pp. 3039-3044.

M. J. DiToro, Low-dispersion wired delay lines,: 1958, IRE National Convention Record, New York, pp. 82-90.

DE19847365 Abstract, May 4, 2000.

* cited by examiner

PROBE SYSTEM, ULTRASOUND SYSTEM AND METHOD OF GENERATING ULTRASOUND

BACKGROUND

The invention relates generally to inspection technology and more specifically, to nondestructive testing techniques using plasma discharge.

Ultrasonic inspection of materials is a commonly used technique for detecting and quantifying material defects and subsurface damage of industrial components. However, one of the limitations of conventional ultrasonic inspection techniques is that a liquid interface between the probe and the material being inspected is necessary to avoid excessive reflection of acoustic energy from the air gap that would otherwise be present at the interface. Non-contact ultrasound inspection is an attractive non-destructive inspection technique, particularly for materials that could be damaged by water, for materials at elevated temperatures, and where the logistics of supplying water at an interface is expensive or difficult. One possible non-contact inspection technique is air-coupled ultrasound. However, air-coupled ultrasound exhibits a relatively poor signal to noise (approximately 40-80 dB less than liquid coupled ultrasound).

Commonly used techniques for generation of ultrasound in materials through air gaps include localized laser heating or ablation of the part surface (laser ultrasound), high power piezoelectric or capacitive membrane devices that are acoustically matched to air, and electromagnetic acoustic transducers (EMATs) that generate mechanical vibrations in the material through electromagnetic force. However, each of these techniques suffers from certain limitations. For example, although laser ultrasound is very effective at generating ultrasound in metals and some composites, it is mildly damaging to the surface of the material and very expensive to implement. As regards conventional high-power air-matched ultrasound transducers and EMATs, it has been observed that these techniques are generally limited in terms of maximum output power.

Hence, there is a need for improved ultrasonic inspection systems that address the aforementioned issues.

BRIEF DESCRIPTION

In accordance with one embodiment, a probe system is provided. The probe system includes an inner conductor coupled to an alternating current (AC) voltage source. The probe system also includes an outer conductor arranged around the inner conductor and coupled at one end to the AC voltage source. The outer conductor forms a first electrode at another end thereof. The probe system further includes a second electrode separated from the first electrode by a gap for initiating a plasma discharge in the gap.

In accordance with another embodiment of the invention, a shielded probe system is provided. The shielded probe system includes a center conductor coupled at one end to an AC voltage source and forming a first electrode at another end thereof. The shielded probe system also includes an outer conductor arranged around the center conductor and coupled at one end to the AC voltage source. The outer conductor forms a second electrode at another end thereof, and the first and second electrodes are separated by a gap for initiating a plasma discharge in the gap. The shielded probe system further includes a shield disposed concentric with the center conductor for electromagnetic interference shielding.

In accordance with another embodiment of the invention, an ultrasound probe system is provided. The ultrasound probe system includes a carrier signal source for supplying a radio frequency (RF) carrier signal. The ultrasound probe system also includes an acoustic modulator for supplying an envelope signal. The ultrasound probe system also includes a mixer for mixing the RF carrier signal and the envelope signal to supply a modulated RF signal. The ultrasound probe system further includes a ground electrode. The ultrasound probe system also includes a radio frequency plasma probe separated from the ground electrode by a gap and configured to receive the modulated RF signal and generate a plasma in the gap. The plasma generates ultrasound waves.

In accordance with another embodiment of the invention, a method of generating ultrasound is provided. The method includes supplying a modulated radio frequency signal to a radio frequency plasma probe. The method also includes initiating a plasma discharge via the radio frequency plasma probe. The method also includes stabilizing the plasma discharge via the radio frequency plasma probe. The method further includes modulating intensity of the plasma discharge. The method also includes generating ultrasound waves using the plasma discharge.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present invention overcomes the above-discussed shortcomings of conventional air-coupled ultrasonic inspection techniques by providing an improved transmitter design having increased maximum acoustic output power deliverable to the part being inspected. In this manner the signal levels of the measurement are increased. As discussed in detail below, embodiments of the present invention include a system for initiating and stabilizing a plasma discharge.

Embodiments of the invention also include an ultrasound system and a method for generating ultrasound waves using the plasma. As used herein, 'plasma discharge' refers to plasma generated at atmospheric pressure and at a radio frequency with a frequency in the range greater than about 1 MHz. The ultrasound waves generated are high pressure acoustic waves used in non-destructive testing to inspect defects and any subsurface damage in a material. The non-destructive testing using ultrasound refers herein to 'air-coupled' ultrasound wherein a probe generating plasma and the material to be inspected are separated by an air gap.

Conventional electronic components used to initiate a plasma discharge have been commonly found to be inefficient in order to achieve the desired voltage for plasma discharge. Moreover, plasma discharges are inherently unstable at atmospheric pressure due to decrease in electrical impedance of the plasma discharge with increasing current. Further, plasma at atmospheric pressure requires high voltages to initiate. Beneficially, the present invention provides a stable, low-intensity narrow-band plasma source at atmospheric pressure in air.

Figure 1:
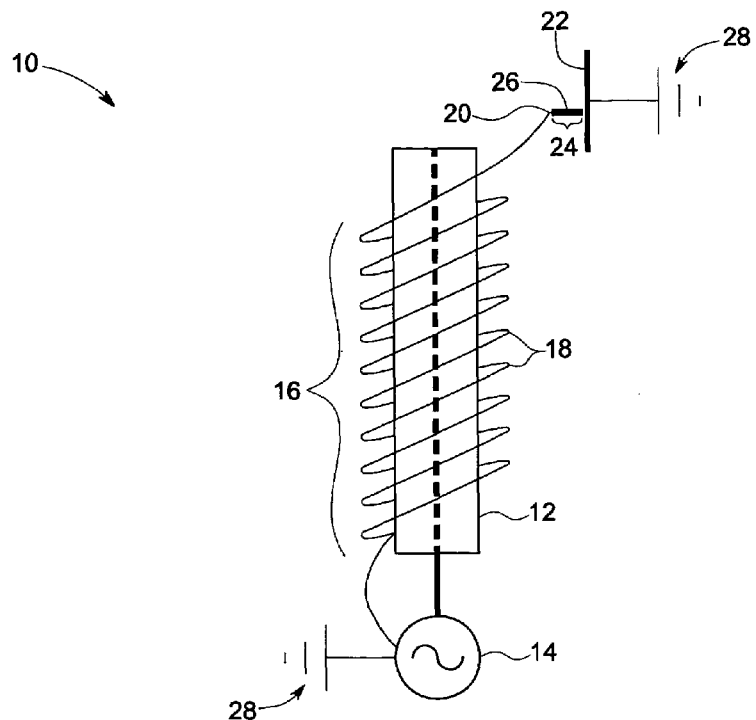
FIG. 1 is a diagrammatic illustration of a system for initiating and stabilizing plasma at radio frequency in accordance with embodiments of the invention.

Turning now to the drawings, FIG. 1 is a diagrammatic illustration of a system 10 for initiating and stabilizing plasma. The system 10 may also be referred to as a plasma probe 10. The plasma probe 10 includes an inner conductor 12 coupled to an alternating current (AC) voltage source 14. For the illustrated embodiment, an outer conductor 16 including multiple windings 18 is arranged around the inner conductor 12. The outer conductor 16 is coupled to the AC voltage source 14 at one end and forms a first electrode 20 at an opposite end. For the illustrated embodiment, a second electrode 22 is separated from the first electrode 20 by a gap 24 for initiating a plasma discharge 26. In a particular embodiment, the inner conductor 12 is a conductor that is cylindrical in shape. In another embodiment, the inner conductor 12 is a wire. In an example, the outer conductor 16 is a solenoid. In an exemplary embodiment, the inner conductor 12 is connected to ground 28. In another embodiment, the outer conductor 16 is connected to ground 28 through the AC voltage source 14. In an example, the plasma discharge 26 may initiate an atmospheric pressure radio-frequency plasma with a frequency in a range between about 6 MHz and about 7.5 MHz. In a particular embodiment, the inner conductor 12 and the outer conductor 16 are configured to step up a voltage supplied by the AC voltage source 14 to initiate the plasma 26 by at least about 20 dB. Although FIG. 1 shows a solenoid 16 that extends around a solid inner conductor 12, in another embodiment (not shown), the inner conductor 12 is a solenoid placed inside the outer conductor 16, which is a solid (for example, hollow tube) metal electrode.

Figure 2:
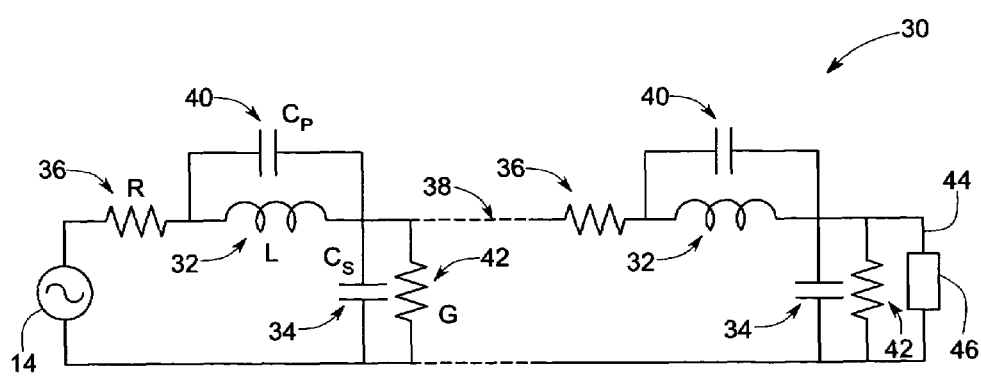
FIG. 2 is an equivalent circuit representation of the system in FIG. 1.

FIG. 2 is an equivalent circuit 30 of the plasma probe 10 in FIG. 1. The inner conductor 12 as referenced in FIG. 1 and the outer conductor 16 as referenced in FIG. 1 are configured as a series LC circuit, where L is the inductance of the outer conductor 16 represented by inductor 32 and $C_s$ is the capacitance between the inner conductor 12 and the outer conductor 16 represented by capacitor 34. The inductor 32 may have a small real value resistance represented by resistor 36. In a particular embodiment, the resistance 36 may vary between about 10 and about 100 ohms. The plasma probe 10 as referenced in FIG. 1 acts as a quarter wave transformer with a distributed transmission line 38 through the inner conductor 12 and the outer conductor 16. The outer conductor 16 may include a large number of windings 18 as referenced in FIG. 1 so as to increase the inductance per unit length. The windings 18 may include a parasitic capacitance 40 between each of the windings 18, which is much smaller than the capacitance 34 denoted by $C_s$. Consequently, the capacitance 40 may be negligible. The electrical circuit 30 may also include a leakage resistance 42 of the capacitance 34 and is denoted by G. The leakage resistance 42 may be very small and hence negligible.

Prior to the plasma being initiated, the AC voltage source 14 sees an open circuit transmission line as there is no load. The equivalent circuit 30 is resonated at a quarter wavelength. Quarter wave resonance occurs when frequency of the source 14 generates a standing wave in the transmission line 38 such that the physical length of the transmission line 38 is a quarter of the wavelength of the standing wave. Thus, the source 14 sees a short circuit at an end 44 of the transmission line 38 resulting in a load 46. This leads to a large amount of current being driven into the transmission line 38. The large current generated passes through the inductor 32 and the capacitor 34. Further, impedance of the inductor 32, which is given by $2\pi fL$ where f is the frequency of the source 14, is large as both L and f are large. Hence, voltage drop across the inductor 32 is large resulting in a high voltage at the end 44 of the transmission line 38. The high voltage initiates generation of plasma at the load 46.

The generation of plasma leads to the transmission line 38 being short circuited at the load 46. In such a scenario, the current driven into the transmission line 38 may have two paths. One of them being through the inductor 32 as described above and the other being through the load 46 bypassing the inductor 32. Thus, the current gets split into two paths with lesser amount of current flowing through the inductor 32. This results in a lower voltage drop across the inductor 32, which is also the voltage through the generated plasma at the load 46. Hence, the current going into the plasma is reduced consequently increasing the plasma resistance. A very fast negative feedback loop is generated thus stabilizing the generated plasma at load 46. Thus, the plasma probe 10 plays an important role in initiating the plasma and then stabilizing the voltage to a desirable value so as not to extinguish the plasma and at the same time preventing any possible burn out.

Figure 3:
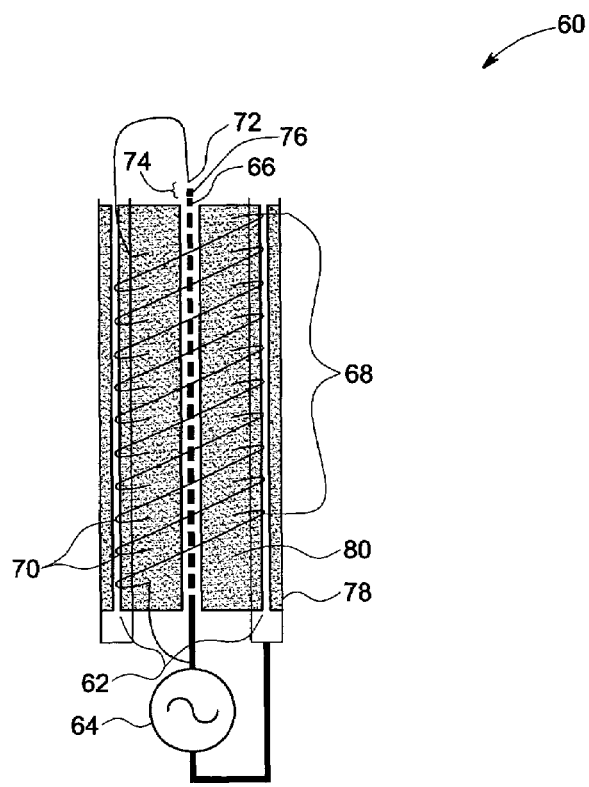
FIG. 3 is a diagrammatic illustration of a shielded probe system for initiating and stabilizing plasma discharge in accordance with embodiments of the invention.

In another illustrated embodiment of the invention, FIG. 3 is a shielded probe system 60 to initiate and stabilize plasma generation. The system 60 includes a center conductor 62 coupled at one end to an AC voltage source 64 and forming a first electrode 66 at an opposite end. The system 60 also includes an outer conductor 68 including multiple windings 70 arranged around the center conductor 62. For the illustrated embodiment, the outer conductor 68 is coupled at one end to the AC voltage source 64 and forms a second electrode 72 at an opposite end. As indicated, the first electrode 66 and the second electrode 72 are separated by a gap 74 to initiate a plasma discharge 76. The system 60 further includes a shield 78 disposed concentric with the center conductor 62 for electromagnetic interference shielding. The magnetic field generated by the outer conductor 68 is compressed and exists in the space between the center conductor 62 and the shield 78. The center conductor 62 and the outer conductor 68 may be configured to step up a voltage supplied by the AC voltage source 64 by about 40 dB. Insulation 80 may be disposed between the center conductor 62 and the shield 78. In a particular embodiment, the insulation 80 is ceramic insulation. In an example, the shield 78 includes an inner conductive cylinder and an outer conductive cylinder that are concentric and connected to one another, and wherein the outer conductor 68 is disposed between the inner and outer conductive cylinders. The shielded probe system 60 initiates a warm plasma discharge 76. As used here, "warm plasma" refers to plasma that is hot enough to burn paper but not so hot as to melt copper. Although FIG. 3 shows a solenoid 68 that extends around center conductor 62, in another embodiment (not shown), the center conductor 62 is a solenoid placed inside the outer conductor 68, which is a solid (for example, hollow tube) metal electrode.

Figure 4:
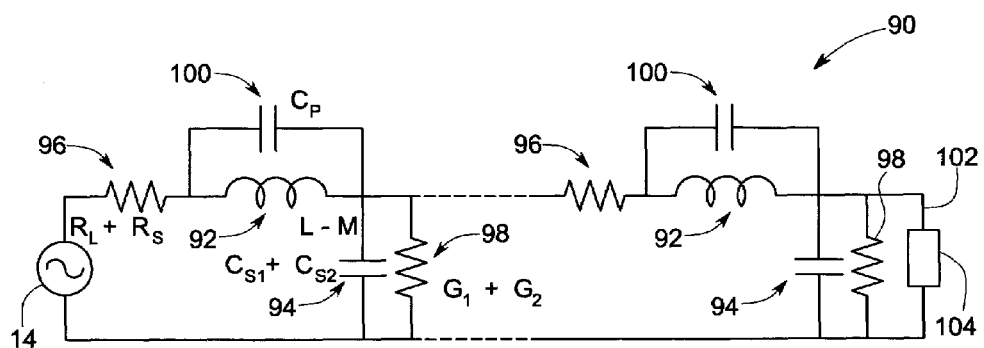
FIG. 4 is an equivalent circuit representation of the shielded probe system in FIG. 3.

FIG. 4 is an equivalent circuit 90 of the shielded probe system 60 in FIG. 3. The center conductor 62 in FIG. 3 and the outer conductor 68 in FIG. 3 are configured as a series LC circuit. The presence of the shield 78 as referenced in FIG. 3 reduces the effective inductance in the circuit 90 and increases the effective capacitance. The effective inductance is equivalent to (L-M) represented by inductor 92, wherein L is the inductance of the center conductor and M is the mutual inductance between the center conductor 62 and the shield 78 due to eddy current losses. The effective capacitance is equivalent to $(C_{s1}+C_{s2})$ represented by capacitor 94, wherein $C_{s1}$ is the capacitance between the center conductor 62 and the outer conductor 68 and $C_{s2}$ is the capacitance between the shield 78 and the outer conductor 68. The inductor 92 may have a small real value resistance represented by resistor 96 that includes resistance due to eddy current losses. The capacitor 94 may include a negligible leakage resistance represented by a leakage resistor 98. The circuit 90 may also include a negligible parasitic capacitance represented by capacitor 100 between each of the windings 70 as referenced in FIG. 3. Since the effective inductance is smaller and there are more losses in the form of eddy currents, the voltage required to initiate a plasma discharge increases. The initiation of a plasma discharge results in a short circuit at an end 102 with a load 104. Hence, this may lead to a lesser efficient plasma probe as compared to the plasma probe described in FIG. 1.

Beneficially, the probes 10, 60 provide a stable, low-intensity narrow-band plasma source at atmospheric pressure in air. The plasma is relatively non-damaging to most industrial materials, such as metals, plastics and composites and does not generate excessive electromagnetic interference. The source is also very efficient and does not require excessively large source voltages to operate. The probes 10, 60 may be used to generate plasma discharges for use at high temperatures to measure gap lengths within an object, such as a turbine engine. In addition, the probes 10, 60 may be used to generate plasma discharges for generating ultrasound waves that may be used to detect defects, as discussed below.

Figure 5:
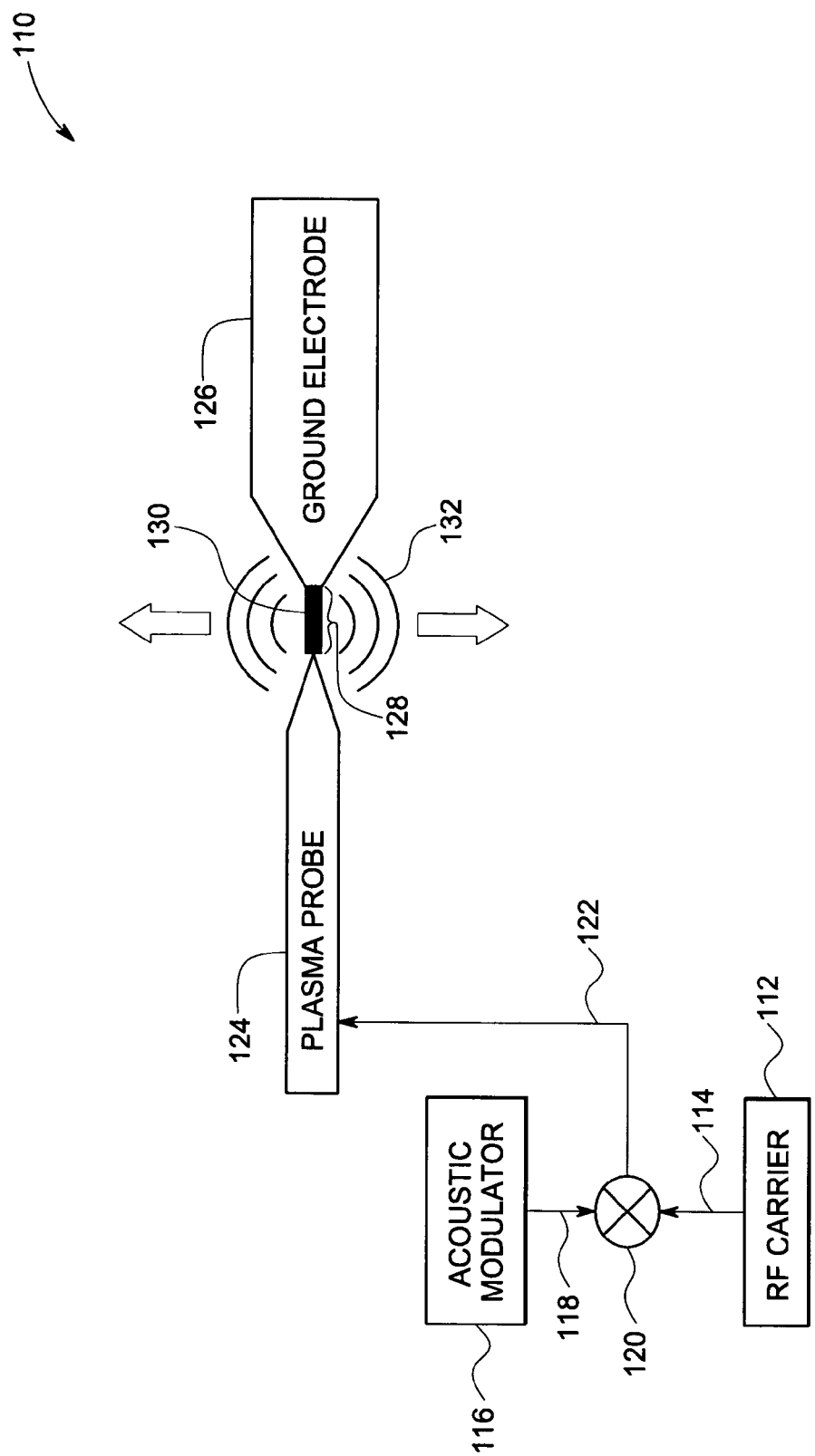
FIG. 5 is a block diagram representation of ultrasound generation using the systems in FIG. 1 and FIG. 2 and a ground electrode in accordance with embodiments of the invention.

FIG. 5 is a diagrammatical illustration of an ultrasound probe system 110. The ultrasound probe system 110 includes a carrier signal source 112 for supplying a radio frequency (RF) carrier signal 114. In a particular embodiment, the frequency of the RF carrier signal 114 may vary in a range between about 10 MHz and about 50 MHz. The system 110 also includes an acoustic modulator 116 for supplying an envelope signal 118. In an example, the acoustic modulator 116 includes at least one function generator configured to supply the envelope signal 118 with a frequency in a range of about 0.001 MHz and about 2 MHz. The ultrasound probe system 110 also includes a mixer 120 for mixing the RF carrier signal 114 and the envelope signal 118 to supply a modulated RF signal 122. In the illustrated embodiment, the modulated RF signal 122 is transmitted to a RF plasma probe 124 separated from a ground electrode 126 by a gap 128. A plasma 130 is generated in the gap 128, which in turn generates multiple ultrasound waves 132. In an example, the RF plasma probe may be an unshielded plasma probe as described in FIG. 1. In another embodiment, the RF plasma probe may be a shielded plasma probe as described in FIG. 3. In a particular embodiment, the gap 128 between the RF plasma probe 124 and the ground electrode 126 is less than about 1 mm. Although FIG. 5 depicts a grounded electrode 126, in another embodiment (not shown), the electrode 126 is not grounded.

Figure 6:
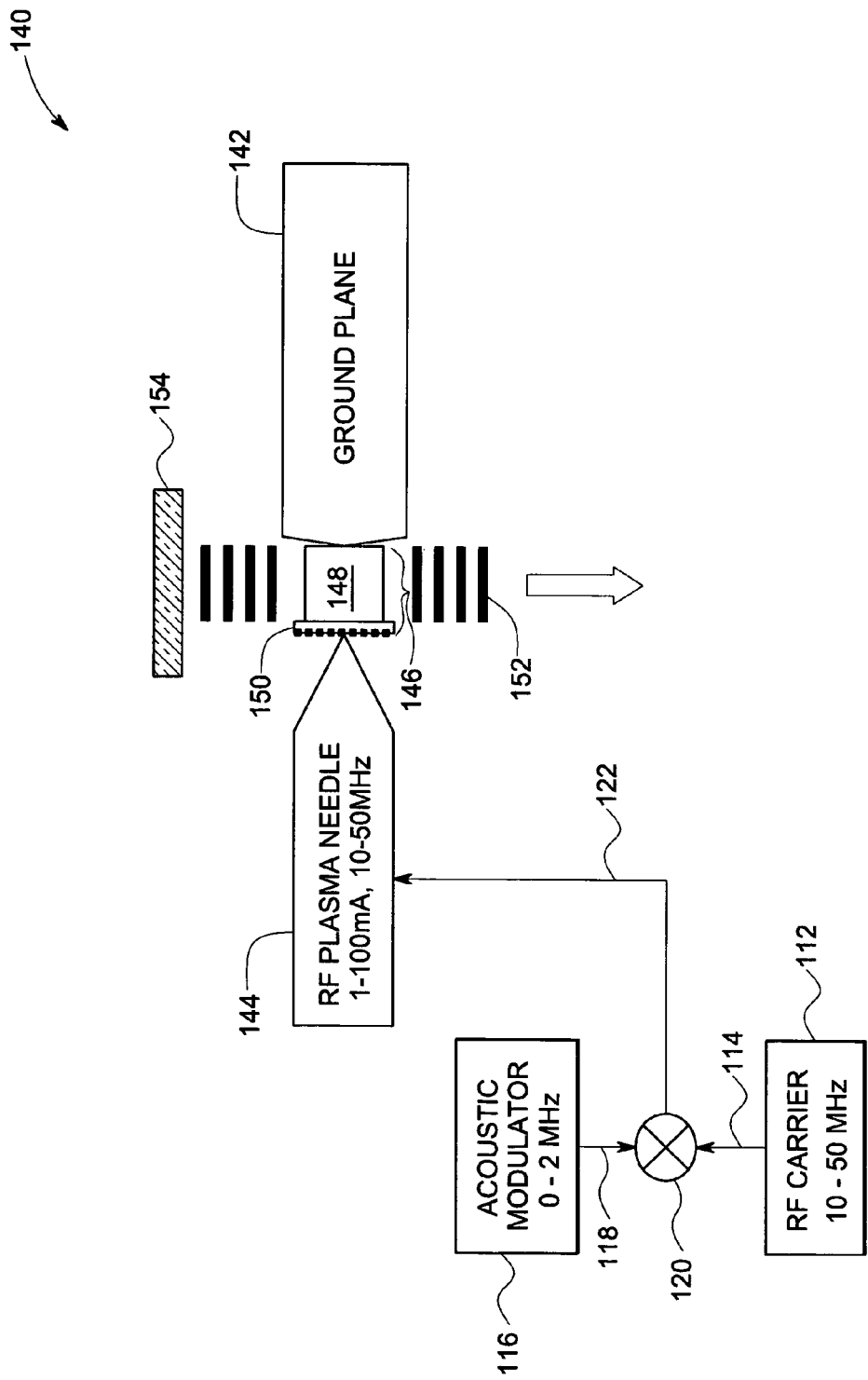
FIG. 6 is a block diagram representation of ultrasound generation using the systems in FIG. 1 and FIG. 2 and a ground plane as an electrode in accordance with embodiments of the invention.

In another illustrated embodiment of the invention as shown in FIG. 6, an ultrasound probe system 140 using a ground plane 142 is depicted. The system 140 includes a carrier signal source 112 as referenced in FIG. 5 for supplying a RF carrier signal 114. In a particular embodiment, the frequency of the RF carrier signal 114 may vary in a range between about 10 MHz and about 50 MHz. The system 140 also includes an acoustic modulator 116 as referenced in FIG. 5 for supplying an envelope signal 118 as referenced in FIG. 5. In an example, the acoustic modulator 116 includes at least one function generator configured to supply the envelope signal 118 with a frequency in a range of about 0.001 MHz and about 2 MHz. The ultrasound probe system 140 also includes a mixer 120 as referenced in FIG. 5 for mixing the RF carrier signal 114 and the envelope signal 118 to supply a modulated RF signal 122 as referenced in FIG. 5. In the illustrated embodiment, the RF carrier signal 122 is transmitted to a RF plasma needle 144 separated from the ground plane 142 by a gap 146. In a particular embodiment, the RF plasma needle may be configured to provide current in a range of about 1 mA and about 100 mA and a frequency in a range of about 10 MHz and about 50 MHz. Plasma is generated in the gap 146. In an example, a dielectric barrier 148 may be disposed in the gap 146 between the RF plasma needle 144 and the ground plane 142. Further, a metal mesh 150 may be disposed on an end of the dielectric barrier 148 facing the RF plasma needle 144. The plasma generated in the gap 146 in turn generates multiple ultrasound waves 152. The system 140 may also include an acoustic mirror 154 that reflects the generated ultrasound waves 152 to increase the efficiency.

Figure 7:
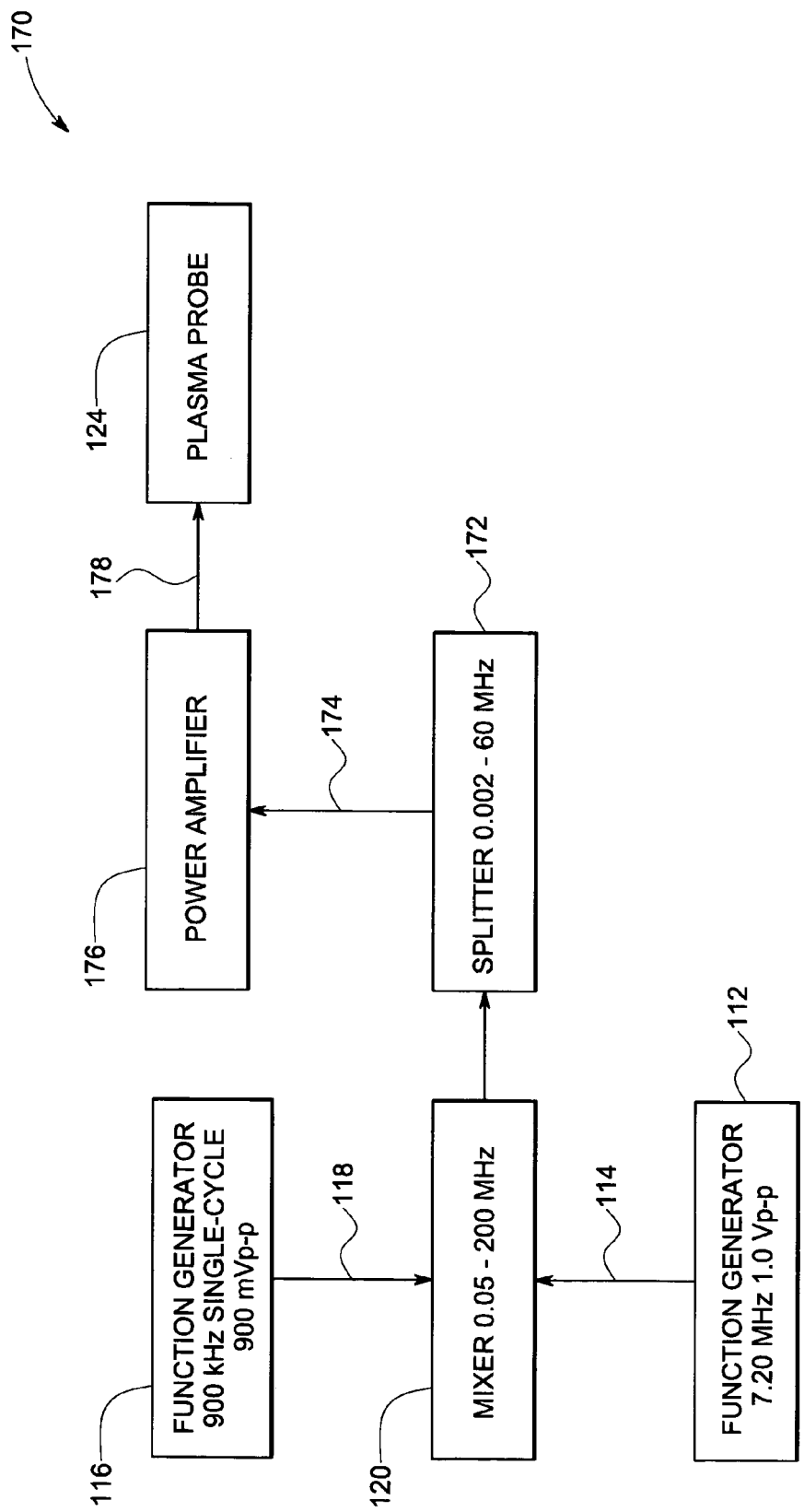
FIG. 7 is a block diagram representation of a signal modulation system used in the ultrasound generation system in FIG. 5 and FIG. 6.

FIG. 7 is a block diagram representation of a signal modulation system 170 in the ultrasound probe system described in FIG. 5 and FIG. 6. The RF signal 114 as referenced in FIG. 5 from the carrier signal source 112 and the envelope signal 118 as referenced in FIG. 5 from the acoustic modulator 116 are fed into the mixer 120. In a particular embodiment, the carrier signal source 112 may be a function generator operating at 7.2 MHz. In another embodiment, the acoustic modulator 116 may be a function generator providing a 900 kHz single cycle sine wave for amplitude modulation. The modulated RF signal 122 from the mixer 120 as referenced in FIG. 5 may be fed into a splitter 172 that provides a RF spectrum signal 174 with a center peak at 7.2 MHz and two side bands at 900 kHz. The generation of such a center peak is useful in maintaining a plasma discharge when an ultrasound wave is not being generated. The RF spectrum signal 174 is fed into a power amplifier 176 that modulates the envelope of the RF carrier signal 122. The modulated envelope signal 178 from the power amplifier 176 is fed into the RF plasma probe 124 as referenced in FIG. 5. When the amplitude of the RF spectrum signal 174 is increased, it results in generation of warm plasma and when the amplitude is decreased, it results in generation of cold plasma. The sudden cooling and heating of the plasma leads to generation of high pressure and low pressure variation of the plasma that leads to propagation of acoustic waves.

Figure 8:
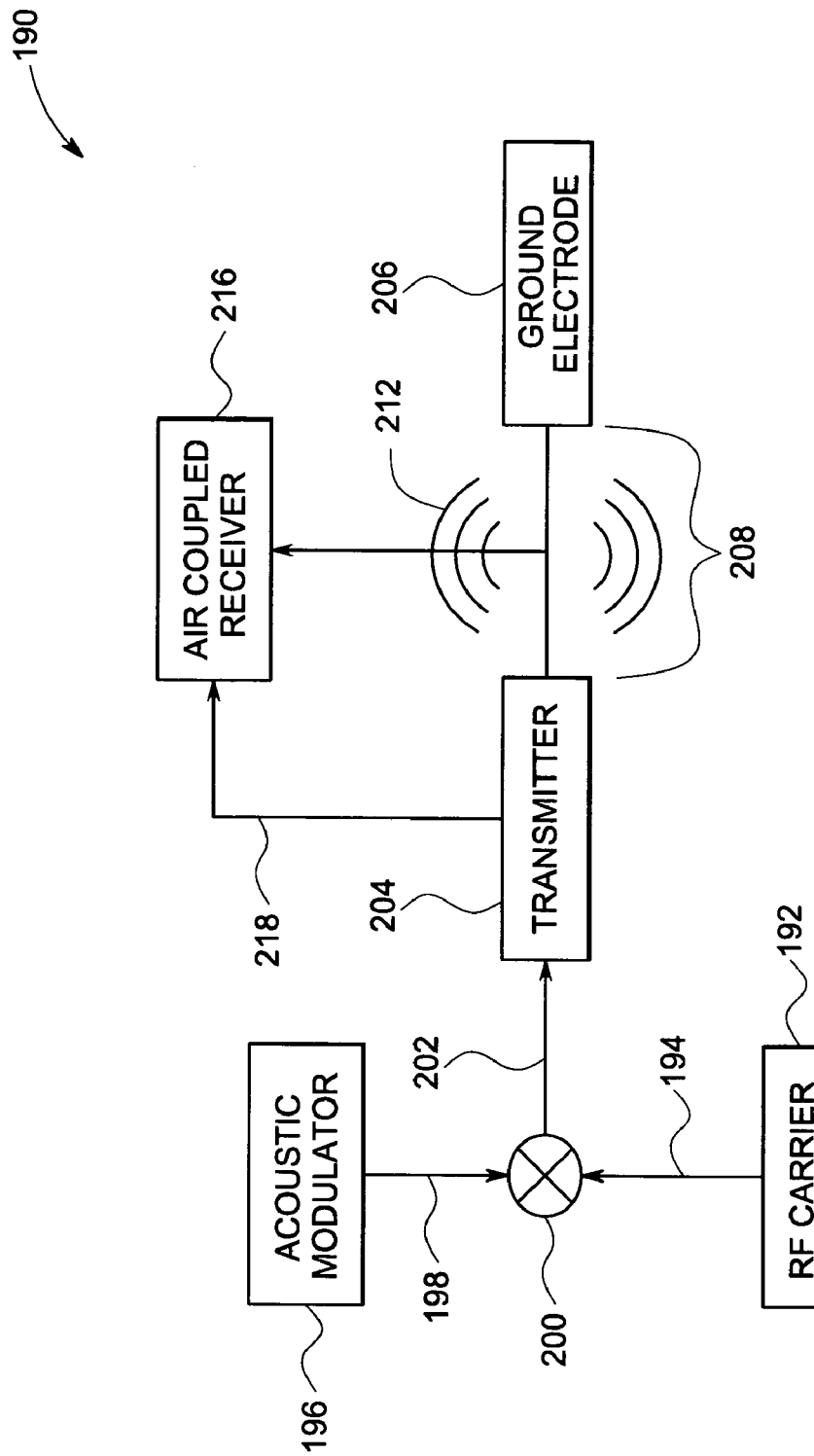
FIG. 8 is a block diagram representation of an air coupled ultrasound receiver system 190 for inspecting an object.

FIG. 8 is a block diagram representation of an air coupled ultrasound receiver system 190 for inspecting an object. The system 190 includes a carrier signal source 192 for supplying a RF carrier signal 194. In a particular embodiment, the frequency of the RF carrier signal 194 may vary in a range between about 10 MHz and about 50 MHz. The system 190 also includes an acoustic modulator 196 for supplying an envelope signal 198. In an example, the acoustic modulator 196 may include at least one function generator configured to supply the envelope signal 198 with a frequency in a range of about 0.001 MHz and about 2 MHz. The air coupled ultrasound system 190 also includes a mixer 200 for mixing the RF carrier signal 194 and the envelope signal 198 to supply a modulated RF signal 202. In the illustrated embodiment, the modulated RF signal 202 is fed to a transmitter 204 separated from a ground electrode 206 by a gap 208. In an example, the transmitter 204 is a RF plasma probe. Plasma is generated in the gap 208, which in turn generates multiple ultrasound waves 212. In an example, the RF plasma probe may be an unshielded plasma probe as described in FIG. 1. In another embodiment, the RF plasma probe may be a shielded plasma probe as described in FIG. 3. In a particular embodiment, the gap 208 between the RF plasma probe 204 and the ground electrode 206 may be less than about 1 mm. The generated ultrasound waves 212 are received by a receiver 216. In the illustrated embodiment, the receiver 216 is separated from the transmitter at an air gap 218. In an example, the air gap 218 may be about 10 mm.

Figure 9:
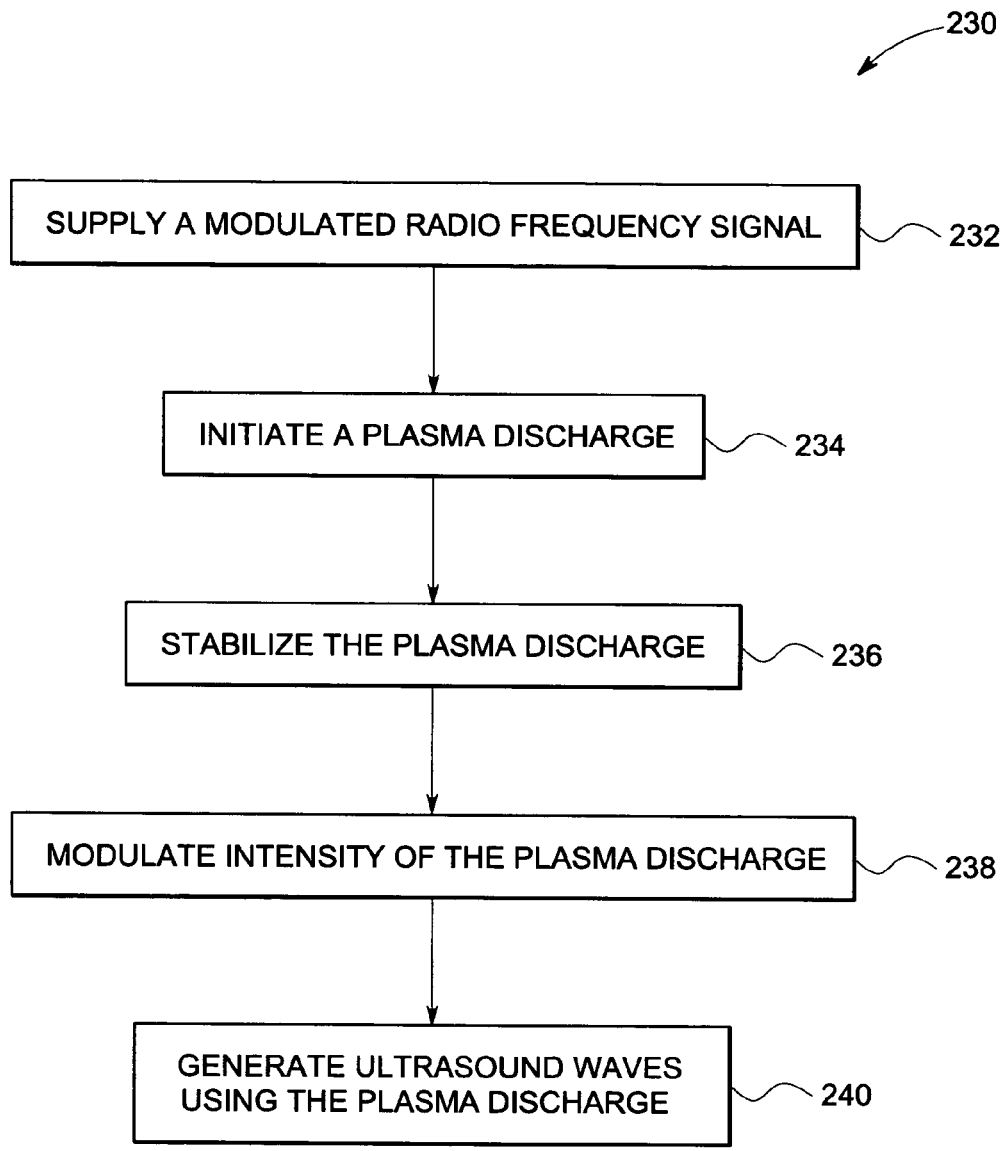
FIG. 9 is a flow chart illustrating exemplary steps for a method of generating ultrasound waves.

FIG. 9 is a flow chart illustrating exemplary steps for a method 230 of generating ultrasound waves. The method 230 includes supplying a modulated radio frequency signal to a radio frequency plasma probe as step 232. The process of supplying a modulated radio frequency signal includes supplying a radio frequency carrier signal, supplying a modulation signal and mixing the modulation signal and the radio frequency carrier signal to form the modulated radio frequency carrier signal. The radio frequency plasma probe initiates a plasma discharge in step 234. Once initiated, the plasma is stabilized by the radio frequency plasma probe in step 236. The stabilizing may include supplying a feedback in the radio frequency plasma probe. The intensity of the plasma discharge is modulated in step 238. In an example, modulating the intensity may include modulating current through the radio frequency plasma probe. The modulation of intensity of the plasma discharge results in generation of multiple ultrasound waves in step 240.

Beneficially, the above described ultrasound system and method of generating ultrasound are capable of generating relatively large amplitude sonic vibrations in air. Further, the above described plasma probes have no practical limitations on acoustic output power, with device efficiencies comparable to existing transducers. Moreover, the above described plasma generation technique is inexpensive relative to laser ultrasound and avoids damaging the part under test because the plasma generation occurs some distance away from the part.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A probe system comprising:
   an inner conductor coupled to an alternating current (AC) voltage source;
   an outer conductor arranged around the inner conductor and coupled at one end to the AC voltage source, wherein the outer conductor forms a first electrode at another end thereof; and
   a second electrode separated from the first electrode by a gap for initiating a plasma discharge in the gap.

2. The probe system of claim 1, wherein the inner conductor comprises a cylindrical conductor, and wherein the outer conductor comprises a plurality of windings arranged around the inner conductor.

3. The probe system of claim 1, wherein the outer conductor comprises a solenoid.

4. The probe system of claim 1, wherein the inner conductor comprises a wire, and wherein the outer conductor comprises a plurality of windings arranged around the inner conductor.

5. The probe system of claim 1, wherein the plasma discharge initiates an atmospheric pressure plasma.

6. The probe system of claim 1, wherein the second electrode is grounded.

7. The probe system of claim 1, wherein the outer conductor is grounded though the AC voltage source.

8. The probe system of claim 1, wherein the plasma discharge initiates a radio-frequency plasma with a frequency greater than about 1 MHz.

9. The probe system of claim 1, wherein the inner and outer conductors are configured to step up a voltage supplied by the AC voltage source by at least about 20 dB.

10. The probe system of claim 1, wherein the inner and outer conductors are configured as a LC circuit, wherein the outer conductor provides an inductance L, wherein a distributed capacitance between the inner and outer conductors provides a capacitance C, and wherein a maximum voltage is developed at the end of the outer conductor forming the first electrode prior to the plasma discharge.

11. The probe system of claim 10, wherein the LC circuit provides a feedback loop for stabilizing a plasma once initiated, wherein the LC circuit is loaded once the plasma is initiated, and wherein loading the LC circuit provides negative feedback for current stabilization.

12. The probe system of claim 10, wherein an operating frequency of the AC voltage source is an odd multiple of a quarter-wave resonance frequency of the LC circuit.

13. The probe system of claim 1, wherein the inner conductor comprises a plurality of windings.

14. A shielded probe system comprising:
   a center conductor coupled at one end to an alternating current (AC) voltage source and forming a first electrode at another end thereof;
   an outer conductor arranged around the center conductor and coupled at one end to the AC voltage source, wherein the outer conductor forms a second electrode at another end thereof, and wherein the first and second electrodes are separated by a gap for initiating a plasma discharge in the gap; and
   a shield disposed concentric with the center conductor for electromagnetic interference shielding.

15. The shielded probe system of claim 14, further comprising an insulation disposed between the center conductor and the shield.

16. The shielded probe system of claim 15, wherein the insulation comprises a ceramic.

17. The shielded probe system of claim 14, wherein the plasma discharge initiates a warm plasma.

18. The shielded probe system of claim 14, wherein the center and outer conductors are configured to step up a voltage supplied by the AC voltage source by about 20 dB to about 40 dB.

19. The shielded probe system of claim 14, wherein the shield comprises an inner conductive cylinder and an outer conductive cylinder, wherein the inner and outer conductive cylinders are concentric and connected to one another, and wherein the outer conductor is disposed between the inner and outer conductive cylinders.

20. The shielded probe system of claim 14, wherein the center and the outer conductors are configured to develop a maximum voltage at the end of the outer conductor forming the second electrode prior to the plasma discharge, wherein the center and the outer conductors are further configured as part of a LC circuit that provides a feedback loop for stabilizing a plasma once initiated, wherein the LC circuit is loaded once the plasma is initiated, and wherein loading the LC circuit provides negative feedback for current stabilization.

21. The shielded probe system of claim 14, wherein the outer conductor comprises a plurality of windings arranged around the center conductor.

22. The shielded probe system of claim 14, wherein the center conductor comprises a plurality of windings disposed within the outer conductor.

23. An ultrasound probe system comprising:
a carrier signal source for supplying a radio frequency (RF) carrier signal;
an acoustic modulator for supplying an envelope signal;
a mixer for mixing the RF carrier signal and the envelope signal to supply a modulated RF signal;
a ground electrode; and
a radio frequency plasma probe separated from the ground electrode by a gap and configured to receive the modulated RF signal and generate a plasma in the gap, wherein the plasma generates a plurality of ultrasound waves.

24. The ultrasound probe system of claim 23, wherein the gap between the radio frequency plasma probe and the ground electrode is less than about 1 mm.

25. The ultrasound probe system of claim 23, wherein the RF carrier signal has a frequency in a range between about 10 MHz and 50 MHz.

26. The ultrasound probe system of claim 23, wherein the acoustic modulator comprises at least one function generator configured to supply the envelope signal with a frequency in a range of about 0.001-2 MHz.

27. The ultrasound probe system of claim 23, further comprising an acoustic mirror configured to reflect the ultrasound waves generated by the plasma.

28. The ultrasound probe system of claim 23, further comprising:
a dielectric barrier disposed in the gap between the radio frequency plasma probe and the ground electrode; and
a metal mesh disposed on an end of the dielectric barrier facing the radio frequency plasma probe.

29. A method of generating ultrasound comprising:
supplying a modulated radio frequency signal to a radio frequency plasma probe;
initiating a plasma discharge via the radio frequency plasma probe;
stabilizing the plasma discharge via the radio frequency plasma probe;
modulating intensity of the plasma discharge; and
generating a plurality of ultrasound waves using the plasma discharge.

30. The method of claim 29, wherein supplying a modulated radio frequency signal comprises supplying a radio frequency carrier signal, supplying a modulation signal and mixing the modulation signal and the radio frequency carrier signal to form the modulated radio frequency signal.

31. The method of claim 29, wherein modulating intensity of the plasma discharge comprises modulating current though the radio frequency plasma probe.

32. The method of claim 29, wherein stabilizing the plasma discharge comprises supplying feedback in the radio frequency plasma probe.

33. An air-coupled ultrasound system for inspecting an object, the system comprising:
a carrier signal source for supplying a radio frequency (RF) carrier signal;
an acoustic modulator for supplying an envelope signal;
a mixer for mixing the RF carrier signal and the envelope signal to supply a modulated RF signal;
a ground electrode;
a transmitter comprising a radio frequency plasma probe separated from the ground electrode by a gap and configured to receive the modulated RF signal and generate a plasma in the gap, wherein the plasma generates ultrasound waves; and
a receiver for receiving ultrasound waves from the object under test, wherein the receiver, the transmitter and the object are air-coupled.

34. The air-coupled ultrasound system of claim 33, wherein the gap between the radio frequency plasma probe and the ground electrode is less than about 1 mm, and wherein the RF carrier signal has a frequency in a range between about 10 MHz and 50 MHz.

35. The air-coupled ultrasound system of claim 33, further comprising an acoustic mirror configured to reflect the ultrasound waves generated by the plasma toward the object.

* * * * *

UNITED STATES PATENT AND TRADEMARK OFFICE
CERTIFICATE OF CORRECTION

PATENT NO. : 7,454,974 B2
APPLICATION NO. : 11/540742
DATED : November 25, 2008
INVENTOR(S) : May It is certified that error appears in the above-identified patent and that said Letters Patent is hereby corrected as shown below:

In Column 8, Line 16, in Claim 7, delete "though" and insert -- through --, therefor.

In Column 10, Line 19, in Claim 31, delete "though" and insert -- through --, therefor.

Signed and Sealed this

Sixteenth Day of June, 2009

JOHN DOLL
*Acting Director of the United States Patent and Trademark Office*